United States Patent [19]

Wiederrich

[11] 4,319,371
[45] Mar. 16, 1982

[54] LEAFCUTTER BEE NEST

[75] Inventor: LeRoy J. Wiederrich, North Havre, Mont.

[73] Assignee: Pollination Technics, Inc., Havre, Mont.

[21] Appl. No.: 82,739

[22] Filed: Oct. 9, 1979

[51] Int. Cl.³ ............................................. A01K 47/00
[52] U.S. Cl. ................................................ 6/1; 6/11
[58] Field of Search .......................... 6/1, 2 R, 10, 11; 119/1

[56] References Cited

U.S. PATENT DOCUMENTS

| | | | |
|---|---|---|---|
| 4,055,911 | 11/1977 | Aylor | 119/1 X |
| 4,185,343 | 1/1980 | Ross | 6/10 |
| 4,195,379 | 4/1980 | Krasnik | 6/11 |
| 4,207,637 | 6/1980 | Niebur | 6/1 |

Primary Examiner—Gene Mancene
Assistant Examiner—Robert P. Swiatek
Attorney, Agent, or Firm—Dowrey & Cross

[57] ABSTRACT

A nest or hive for bee culture having spirally wound alternate layers of flat and corrugated materials respectively and contained within a predator and parasite resistant holder for attachment to a field support structure.

2 Claims, 3 Drawing Figures

LEAFCUTTER BEE NEST

BACKGROUND OF THE INVENTION

It has been found that the output of seed from alfalfa is greatly increased if the alfalfa is pollinated by insects and the insect most effective for pollination of seed alfalfa is the leafcutter bee. While the leafcutter bee occurs naturally in several areas of the Western United States, domestication of the bee is in wide practice today and requires the construction of artifical nests to increase the number of bees that are present in a given area. In the construction of such nests or hives the following factors must be considered: (1) initial cost, (2) ease of cleaning and larvae removal, (3) resistance to predators and parasites. By balancing and optimizing the above factors, an economically practical nest may be constructed.

Low cost of construction of leafcutter bee nests is essential in that a large number of nests must be provided for fields of even moderate size. Since the leafcutter bee is gregarious and nests in holes in many materials, a nest of very low initial cost has been constructed by simply drilling a plurality of holes of the proper depth in wooden blocks. The female bee partitions the holes into several cells and lays an egg in each cell. The optimum depth of these holes has been found to be approximately four inches, which results in the last or lowest three cells in the hole containing female eggs—the female bee only being responsible for pollination of alfalfa. Similar low cost nests have been constructed from boxes of paper drinking straws or grooved boards held in frames. Nests of these types are generally discarded at the end of each season because of their initial low costs and because of the difficulty in cleaning. Nests of higher initial cost are justifiable only if the nest is reusable within the season and from season to season. For the above reasons, the current trend in the construction of leafcutter bee nests has been toward synthetic materials that are reusable in spite of their somewhat greater initial cost.

The second factor mentioned, i.e., ease of cleaning and larvae removal, has become more important with the increase in demand for bee pollination of alfalfa. In general, after the eggs have been hatched and the young bees have left the nest, the cells of the nest are still filled with debris which may be removed to prevent the growth of fungus and to make way for new nesting holes. Such means as sandblasting and mechanical devices for scraping the interiors of the cells in nests constructed of grooved boards, for example, have been developed. The development of mechanical cleaning means has led to the practice of removing immature larvae from the cells and incubating the larvae under artificial heat. The incubation of the larvae allows control of pests and also allows a larger number of generations of bees to be propagated from a given number of nests in a given season. A mechanical nest cleaning and larvae removal apparatus for nests of the spirally wound type is illustrated in my copending U.S. patent application filed concurrently herewith.

The final factor, that of resistance to predators and parasites, is perhaps the most important. The nests may be attacked by a number of predators which include rodents, as well as insects which burrow into and can destroy the nest itself. Destruction of the physical materials of the nest also destroys the developing bees within the cells with the nest destroyers frequently eating immature leafcutting bees. Insecticides are generally impractical for use in controlling this type of predation due, of course, to the possibility of injury to the leafcutter bees themselves. One of the most destructive insect parasites is a small wasp (Monodontomerus obscurus) which lays eggs in the cells of the leafcutter bee nests, which hatch into larvae that destroy the developing leafcutter bee larvae. The wasp generally attacks the hindmost cell of the nest from behind and can therefore destroy as much as one-third of the useful production of the bees, i.e., the female larvae. A nest should therefore be preferably impenetrable to these types of predators and parasites.

SUMMARY OF THE INVENTION

The nest or hive of the present invention includes an insect and predator impenetrable support housing that attaches the hive to a structural beam in a field shed or the like. This housing encloses the hive except for entry openings, thus preventing the entry of burrowing pests, parasites and other field predators that would otherwise destroy the nests and bee larvae within. The hive itself is located within the interior of the housing and is formed from spirally wound strips of corrugated and flat materials which provide holes in which the bees construct cells containing the eggs which hatch into bee larvae. The holes are formed by the flutes of the corrugated material and the adjacent surface of the flat or separator strip. For cleaning and larvae removal, the spirally wound hive is unwound on a suitable cleaning apparatus such as described in my copending U.S. patent application. Two such spirally wound nests may be placed in a single support housing in back-to-back relation with an intervening layer of material which acts as a barrier which prevents entry of parasites and predators from the rear of the hive.

With this construction, the hives may be used by the bees from both sides. The open construction of the hive allows for air passage through the holes or tunnels provided by the flutes of the corrugated strip and through the foam backing resulting in temperature moderation and moisture dissipation, thus greatly reducing the change of mold and other forms of fungus growth.

DETAILED DESCRIPTION OF THE DRAWINGS

Figure 1:
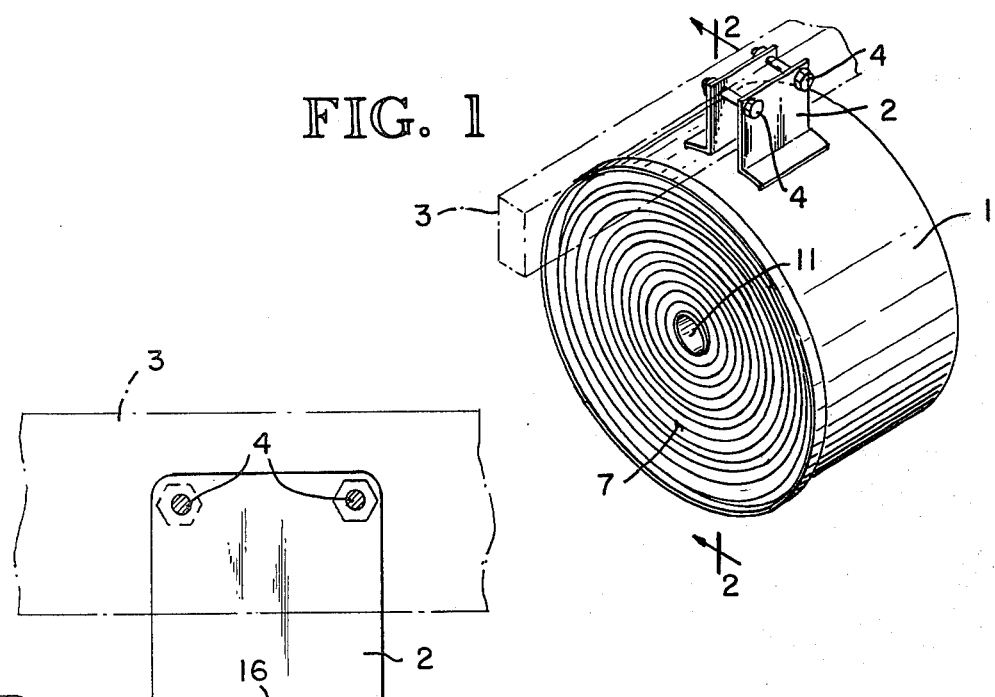
FIG. 1 is a perspective view of a preferred embodiment of the invention.

As used throughout this specification, the term nest will be understood to be synonymous with the term hive and, as will presently be explained, a nest or hive may be a simple or a compound structure involving a plurality of spirally wound nesting units. As illustrated in FIG. 1, the hive of the present invention comprises a cylindrical housing indicated generally at 1 provided with a pair of brackets 2 for attaching the hive housing to a beam or other structural member 3. The beam 3 will normally be a supporting member contained within a shed or other protective structure (not shown), located in the vicinity of the alfalfa field. The purpose of the shed, is, of course, to provide shade, rain cover and support for the bee hives and it will be understood that a number of hives may be located within any support shed as desired. The shed is preferably an open-sided structure which allows for free ventilation about the hive structures and free access by the bees. The brackets 2 may be attached to the beam 3 as by the bolts 4 and, if desired, may be designed so as to be locked to the beam in order to prevent theft. The brackets 2 are fixably connected to the housing 1 so as to prevent removal.

The hive shell or housing 1 of the presently described embodiment is designed to accommodate two individual spirally wound nest units 6 and 7 respectively which may be essentially identical in structure. As aforementioned, the spirally wound nest unit is constructed by winding or wrapping a corrugated strip 8 and a separator strip 9 on any suitable core structure such as the core 11 illustrated in FIG. 1. As illustrated most clearly in FIGS. 2 and 3, the corrugated strip 8 forms a plurality of adjacent holes or tunnels 12 defined by the flutes of the corrugated strip and the surfaces of the separator strip 9. These holes or tunnels provide access for constructing the larvae containing cells as previously described.

The corrugated strip may be fabricated from any suitable material which is sufficiently flexible to be wound in the spiral formation and durable enough to withstand unwinding, cleaning and rewinding. Additionally, the corrugated material should be mold and mildew resistant and capable of withstanding extremely high temperatures such as experienced in the Western and Southwestern United States. Synthetic polymers have been found to be especially adapted for this use and the preferred polymer is ABS copolymer. For the same reasons, the separator strip should be flexible, mold and mildew resistant, and unaffected by the hot climate. Additionally, the separator strip should be sufficiently porous to permit breathing and to be water vapor permeable for the evaporative cooling effect. The preferred material is a foamed synthetic polymer having these properties. In practice, the foam material may be approximately 3/16 inch in thickness and the flutes of the corrugated strip 8 may have a radius of approximately ¼ inch. As aforementioned, the width of the strips 8 and 9 will be in the neighborhood of four inches providing a hole of that depth for producing the optimum ratio of female to male larvae. It will be understood by those skilled in the art, of course, that other equivalent materials may be used as components for the nest.

Figure 2:
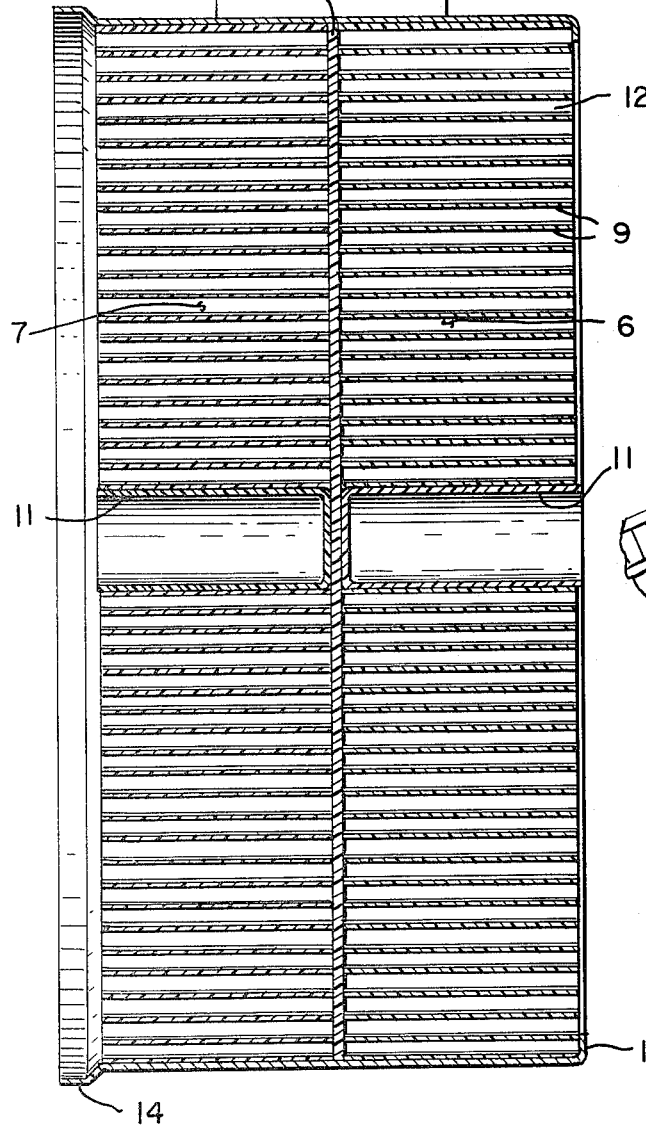
FIG. 2 is a cross-sectional view taken along line 2—2 of FIG. 1.
Figure 3:
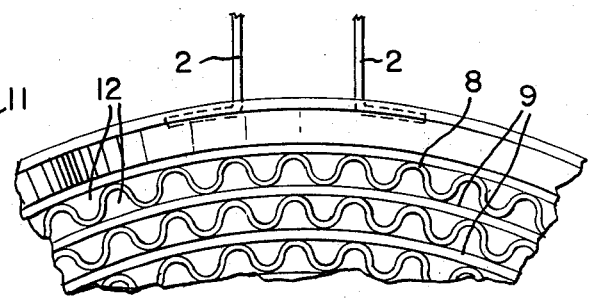
FIG. 3 is an elevation detail of a peripheral portion of the hive.

Referring now to FIG. 2, the shell or hive housing 1 may comprise a right circular cylinder and is preferably constructed of metal such as aluminum or other lightweight material so as to be impenetrable to insects and rodents. Additionally, the cylindrical shape of the shell provides protection against rodents since its curved surface provides no footing convenient for entering the nest. The housing 1 also includes an angular lip or flange 13 on one end and a bell-shaped flange 14 on the opposite end. With this construction, two nest units 6 and 7 may be placed back-to-back with the unit 6 being constrained by the flange 13. The bell flange 14 permits easy assembling of the nesting units. The placement of the two nesting units 6 and 7 as shown in FIG. 1 provides for open access to each of the nesting units from opposite sides of housing 1. In order to prevent migration of parasites from the holes in one nesting unit to the backside of the adjacent nesting unit, a separator member in the form of a disc 16 is located between the nesting units. This separator disc is preferably constructed from a foamed synthetic polymer material similar to the separator strip 9 and of a suitable thickness so as to prevent passage of insects and other parasites.

The novel nest structure of the present invention performs several unique functions. As aforementioned, the most common destructive enemy of the leafcutter bee is a parasitical wasp, which lays eggs in occupied cells of the nest. The wasp eggs hatch into larvae which destroy the developing bee larvae and its food supply. In the nest structure of the present invention, entry to the rear cells of the nest is prevented by the back-to-back arrangement and the protective separator disc. With this arrangement, the wasp would have to penetrate all of the cells of the hole or tunnel to reach the rear cells which contain the female bee larvae. In addition, the wasp is exposed to attack by the leafcutter bees which leave and enter through the front face of the nest. If a wasp happens to enter an unoccupied tunnel, the separator disc 16 prevents his entry into the adjacent nest. As a result, there is a much improved survivability of bees in areas of infestation by this wasp. It is readily apparent also that the construction of the nest or hive is such that sufficient ventilation is provided at all times to prevent the temperature from rising in the portion of the nest to a point which is harmful to the bees. The materials may also be chosen in the preferred embodiment to discourage the support and growth of fungi which are harmful to the bees and limit reusability of the nest.

Further advantages of the double-layered spirally wound nest structure is its adaptability to cleaning and reuse, both because of the structural arrangement and materials chosen. The construction described may be cleaned and sterilized as desired by unwinding the corrugated and separator strips and mechanically removing the bee larvae and nesting debris. The strips are then rewound to reform the nesting unit. Apparatus and method for this operation are disclosed and claimed in my copending application.

Although the present invention has been described with reference to a particular embodiment thereof, it will be understood by those skilled in the art that numerous modifications may be made without departing from the scope of the invention. Accordingly, all modifications and equivalents may be resorted to which fall within the scope of the invention as claimed.

I claim:
1. A bee culture nest comprising in combination:
two nesting units of generally circular cross-section coaxially aligned with one another, each such unit having front and rear surfaces with a plurality of nesting tunnels extending between said front and rear surfaces, said nesting units including:
a first spirally-wound strip of corrugated material and a second spirally-wound strip of flat material interleaved in face-to-face relation with said first strip, said tunnels being formed by the interleaving of said two strips,
a cylindrical housing for supporting said two nesting units and maintaining them in said coaxial alignment, and
separator means between said two nesting units comprising a flat disk of porous foamed synthetic polymer.
2. A bee culture nest comprising:

a nesting unit of generally circular cross-section having front and rear faces and a plurality of nesting tunnels extending between said front and rear faces;

barrier means for closing one end of said tunnels and for permitting air passage therethrough while forming a barrier to the penetration of parasites, said barrier means comprising a generally circular disk of porous foamed synthetic polymer material; and a generally cylindrical housing for enclosing the nesting unit and maintaining the barrier means in contact with the rear face of the nesting unit.

* * * * *